United States Patent
Yimin

Patent Number: 6,102,899
Date of Patent: Aug. 15, 2000

[54] DISPOSABLE TRAINING DIAPER

[76] Inventor: Theresa M. Yimin, 2160 Greentree Rd., Pittsburgh, Pa. 15220

[21] Appl. No.: 09/104,658

[22] Filed: Jun. 25, 1998

[51] Int. Cl.⁷ .................................................. A61F 13/15
[52] U.S. Cl. ...................................... 604/385.01; 604/389
[58] Field of Search ............................ 604/385.1, 395, 604/348, 384; 602/67–73; 2/75, 78.2, 80, 400, 408, 912, 914, 920

[56] References Cited

U.S. PATENT DOCUMENTS

| | | | |
|---|---|---|---|
| 1,853,396 | 4/1932 | Atherton | 2/78.2 |
| 2,837,095 | 6/1958 | Stevenson | 604/395 |
| 3,316,911 | 5/1967 | Barr | 604/348 |
| 4,205,679 | 6/1980 | Repke et al. | 604/385.2 |
| 4,446,575 | 5/1984 | Davis | 2/400 |
| 4,610,680 | 9/1986 | LaFleur | 604/385.2 |
| 4,835,795 | 6/1989 | Lonon | 2/408 |
| 4,906,243 | 3/1990 | Dravland | 604/394 |
| 4,930,161 | 6/1990 | Cohen | 2/408 |
| 4,944,733 | 7/1990 | Casale | 604/385.1 |
| 4,951,321 | 8/1990 | Mortensen et al. | 2/408 |
| 5,137,525 | 8/1992 | Glassman | 604/385.2 |
| 5,207,663 | 5/1993 | McQueen | 604/395 |
| 5,341,515 | 8/1994 | Cohen | 2/78.2 |
| 5,383,867 | 1/1995 | Klinger | 604/395 |
| 5,546,608 | 8/1996 | Russano | 2/408 |
| 5,568,128 | 10/1996 | Nair | 340/604 |
| 5,569,229 | 10/1996 | Rogers | 604/395 |
| 5,624,420 | 4/1997 | Bridges et al. | 604/385.2 |
| 5,636,387 | 6/1997 | Lundy | 607/385.1 |

Primary Examiner—John G. Weiss
Assistant Examiner—K. M. Reichle
Attorney, Agent, or Firm—Law Offices of K. Patrick McKay

[57] ABSTRACT

A disposable training diaper which is an aid to toilet training youngsters, particularly those who may suffer from insecurity as to where feces should be deposited. The toddler is led to believe that the fecal matter is being deposited in the diaper. As the toddler is so believing, the fecal matter is deposited in the toilet because a flap on the underside of the diaper is opened when the toddler is seated on the toilet. Once the toddler realizes it has been deposited in the toilet, the toddler is shown the result, rewarded and the activity is thereby favorably reinforced.

1 Claim, 5 Drawing Sheets

DISPOSABLE TRAINING DIAPER

BACKGROUND OF THE INVENTION

1. Field of the Invention

The present invention, a disposable training diaper, is an aid to toilet training youngsters, particularly those who may suffer from toilet trauma, an insecurity where a toddler perceives that feces should be deposited only in a diaper. The invention herein described overcomes that trauma by a deceptive mechanism whereby the toddler is led to believe that the fecal matter is being deposited in the diaper. As the toddler is so believing, the fecal matter is deposited in the toilet because a flap on the underside of the diaper is opened when the toddler is seated on the toilet. Once the toddler realizes it has been deposited in the toilet, the toddler is shown the result, rewarded and the activity is thereby favorably reinforced.

2. Description of the Related Art

The use of disposable diapers is well known in the art. Separately, the use of training diapers and toddler briefs is also well-taught. The present technology in diapers is utilized throughout the industry. This technology involves the standard diaper being a plastic layered material with absorbent padding sandwiched between the innermost and outermost layers.

In addition, the use of training diapers which are disposable is also in the art, but these diapers are particularly limited to the training of toddlers in urination and not in the depositing of fecal excrement, as described by the present invention.

There is, therefore, a particular need for a disposable diaper that is used to reinforce the activity of toilet training. Specifically, there is a need for a diaper which gives a parent the means to instruct a toddler that the deposition of fecal matter into a toilet is a favorable result.

PRIOR ART

U.S. Pat. No. 5,568,128 (Nair), dated Oct. 22, 1996, instructs in diaper and training pants.

U.S. Pat. No. 4,906,243 (Dravland), dated Mar. 6, 1990, shows a garment which is a combination diaper and training pants which includes a compartment for containing waste.

U.S. Pat. No. 4,944,733 (Casale), dated Jul. 31, 1990, teaches the use of a retractable flap with respect to the male anatomy to allow urination.

SUMMARY OF THE INVENTION

The objective of the present invention is to provide a disposable training diaper which can be used to toilet train a toddler to deposit fecal excrement into a toilet.

A secondary objective is to provide a device, as above, but for particular use as an instructional aid.

A third objective is to provide a device, as above, which is particularly readily available without significant added cost over that of a standard diaper.

The present invention satisfies these objectives, as shall be set forth herein, by teaching a diaper that trains a toddler to deposit fecal excrement into a toilet. The diaper generally comprises a rectangular front portion having an outer face and an inner face, and a rear portion with two long sides, two narrow sides, an outer face and an inner face. A means for releasably fastening the front portion to the rear portion is applied to the inner face of the rear portion at each of the two narrow sides whereby the means for releasably fastening is utilized when the diaper is worn by the toddler. A three-sided retractable flap has a perimeter defined by perforations through the rear portion and is formed by a portion of the rear portion between the perforations. It is centered between the two narrow sides and situated abutting one of the long sides and has an adhesive strip on an outer face thereof permitting the retractable flap to be restrained in an up position. The toddler can then sit on the toilet wearing the diaper having an exposed anal area, and be tricked into depositing the fecal excrement into the toilet, be rewarded for doing so and thus favorably reinforce such depositing.

DETAILED DESCRIPTION OF THE PREFERRED EMBODIMENT

The invention will now be described in detail in relation to a preferred embodiment and implementation thereof which is exemplary in nature and descriptively specific as disclosed. As is customary, it will be understood that no limitation of the scope of the invention is thereby intended, and that the invention encompasses such alterations and further modifications in the illustrated device, and such further applications of the principles of the invention illustrated herein, as would normally occur to persons skilled in the art to which the invention relates.

Figure 1:
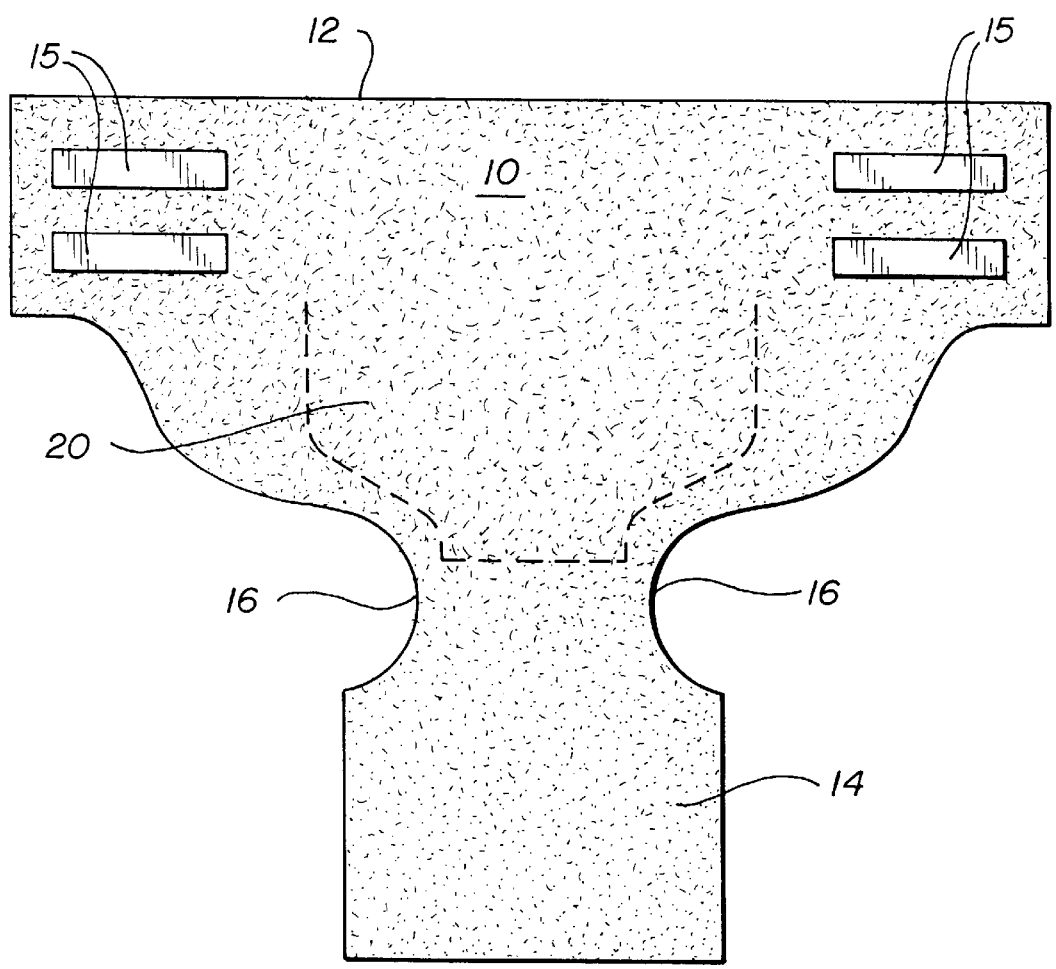
FIG. 1 is a plan view of the disposable training diaper, opened up to show the constituent parts, as viewed from the inside of the diaper.

FIG. 1 demonstrates the disposable training diaper 10 spread apart to demonstrate the constituent parts. In this mode, rear portion 12 has various appurtenant structures that distinguish the present invention and its use. The front portion 14 is generally as fashioned in prior art disposable diapers. The rear portion 12 having generally two long sides 12a, and two narrow sides 12b and front portion 14 are joined at the leg openings 16. The rear portion contains a plurality of adhesive strips fasteners 15 as a means for releasably fastening said front portion 14 to said rear portion 12 and a three-fold retractable flap 20.

Figure 2:
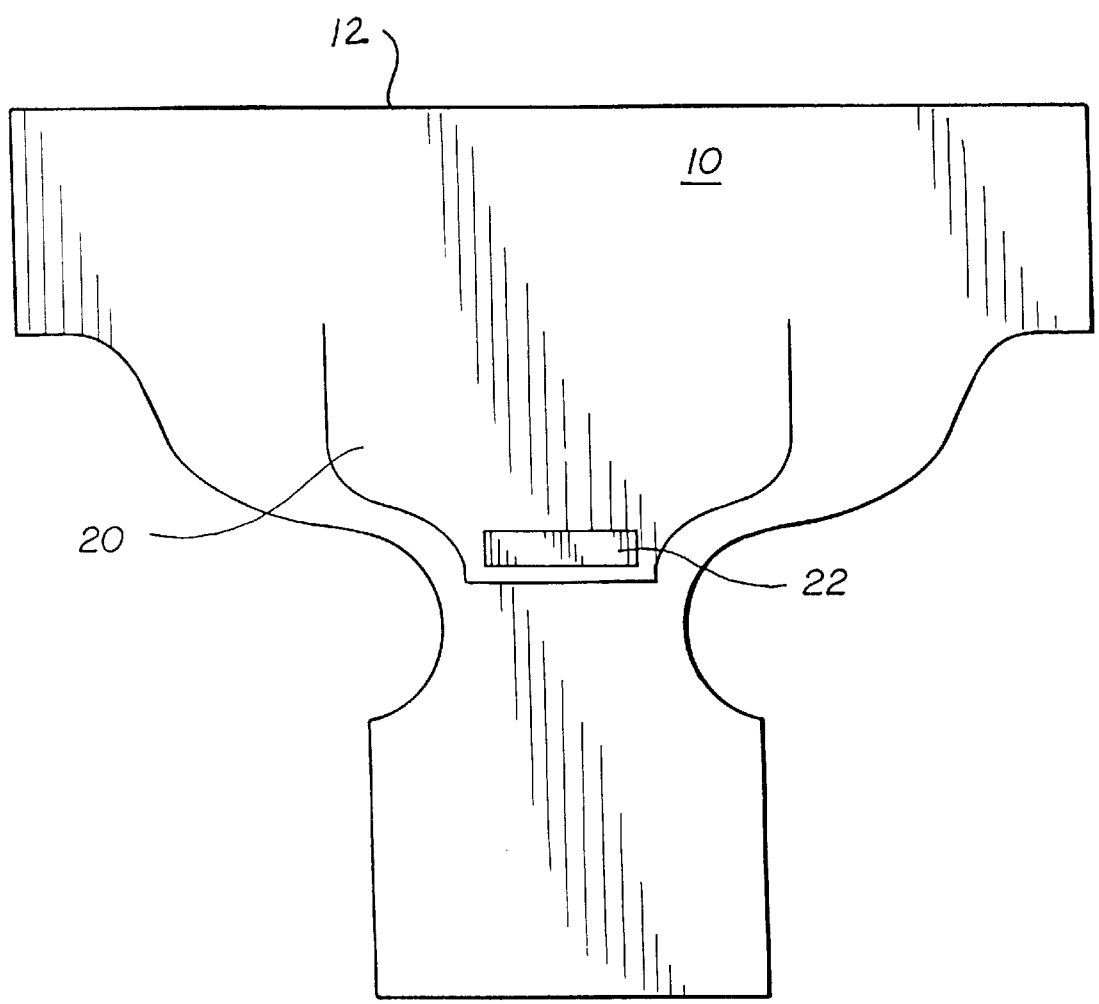
FIG. 2 is a view of the disposable training diaper showing the diaper having a retractable flap in the down position, as viewed from the outside of the diaper.

FIG. 2. shows the disposable training diaper 10 and the rear portion 12 having a retractable flap 20. The retractable flap 20 has a holding adhesive strip 22 which restrains the retractable flap 20 when it is raised for use. The disposable training diaper 10 provides a sense of security for the toddler user. Most often the toddler is accustomed to depositing fecal excrement within the diaper, but as the toddler develops in age, he or she must learn that the correct deposition of fecal excrement is into a toilet. But the toddler often fears the waste being spread outside the diaper. The toddler may then be "tricked" into depositing the waste into the toilet, then rewarded for doing so, thereby justifying his actions and reinforcing the future toilet use.

Figure 3:
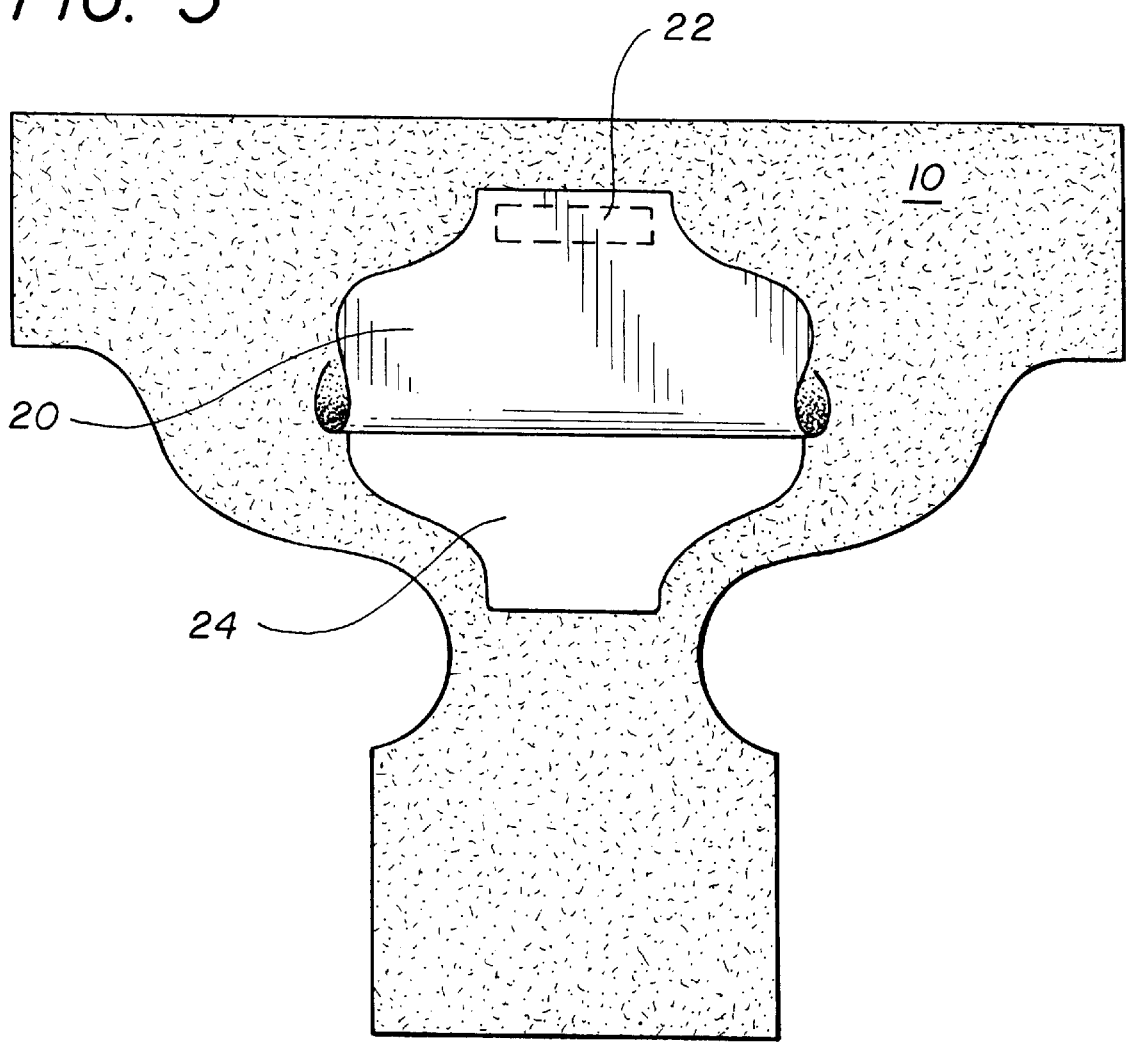
FIG. 3 is a view of the disposable training diaper showing the diaper having a retractable flap in the up position which allows the direct deposition of waste into a toilet as the wearer, a toddler, sits on the toilet.

FIG. 3 shows the disposable training diaper 10 in the view with retractable flap 20 in the up position to reveal a hole 24, and, being restrained by holding adhesive strip 22, thereby exposing the anal area for the toddler to deposit the fecal excrement into the toilet. The retractable flap 20 can be put in the up position by moving the flap upwards where the perforations defining the perimeter 20a are continuous as shown in the Figures or by tearing away the flap from the remainder of the diaper where the perforations defining the perimeter 20a are noncontinuous (not shown) and moving the flap upward.

Figure 4:
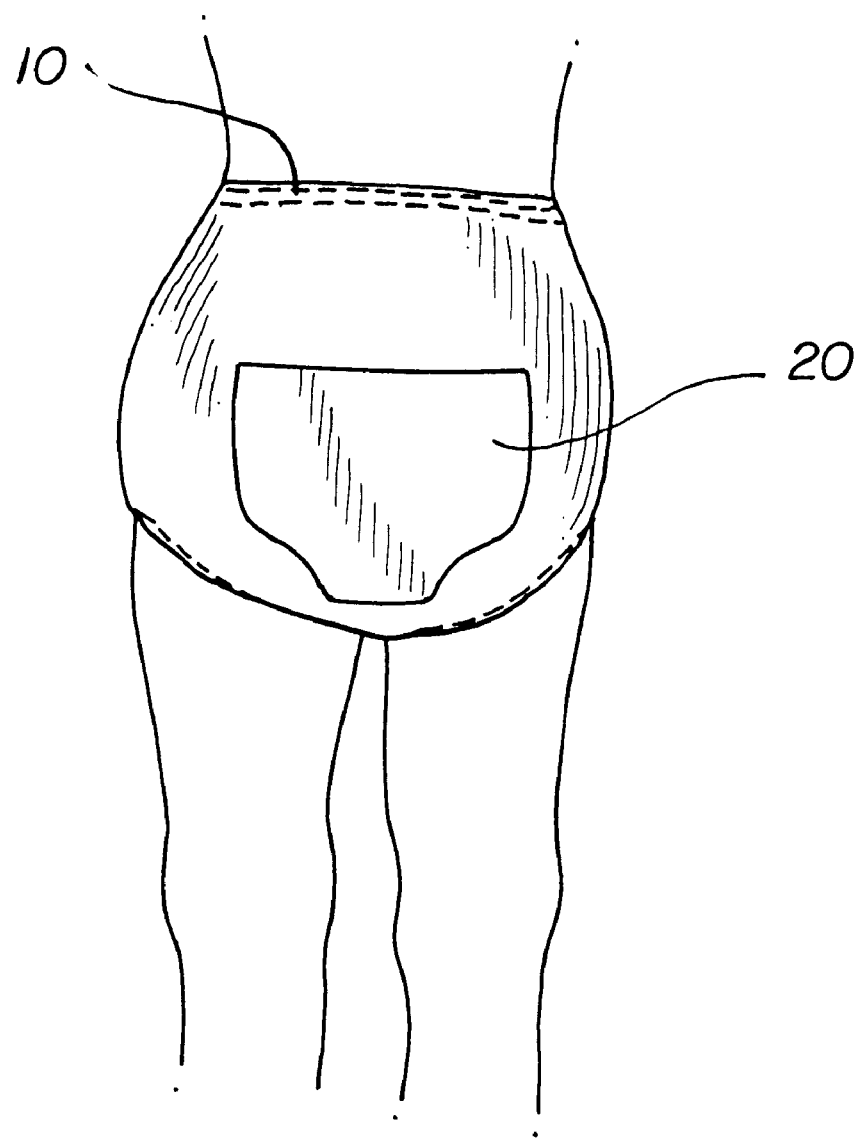
FIG. 4 is a view of the disposable training diaper showing the diaper being worn, from the rear of the toddler.

FIG. 4 shows the disposable training diaper 10 in the view with retractable flap 20 in the down position with adhesive strip 22 unused and anal area 25 unexposed, as the toddler uses the diaper for its normal use. The normal use of a diaper entails the toddler putting his legs through leg openings 16 (see FIG. 1) around a crotch portion 10a disposed between and integral with a front and rear portion to be connected to envelop a toddler's underside.

Figure 5:
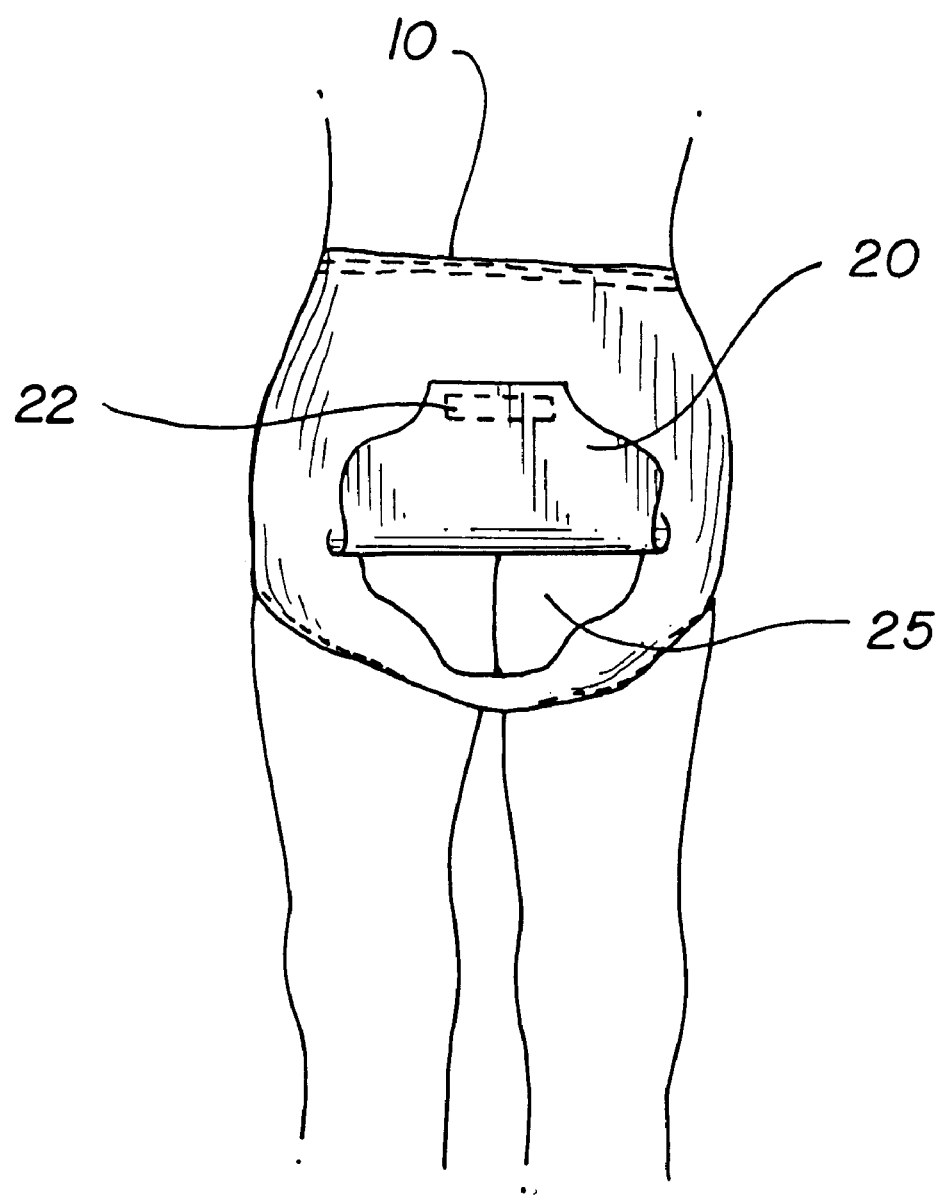
FIG. 5 is a view of the disposable training diaper showing the diaper being worn, from the rear, with the retractable flap up, thereby exposing the anal area of the toddler.

FIG. 5 shows the disposable training diaper 10 in the view with retractable flap 20 in the up position, as the toddler uses the diaper for its special use, thereby exposing the anal area 25, The retractable flap 20 is held in place by holding adhesive strip 22.

The preferred embodiment incorporates into the present invention the complete range of sizes of diapers, from large to small. This mode also incorporates the known art of construction including the various fabrics and absorbent materials and the fastening mechanics for holding the diaper in place.

I claim:

1. A disposable, absorbent diaper for training a toddler to deposit fecal excrement into a toilet, comprising:

(a) a rectangular front portion having an outer face and an inner face;

(b) a rear portion with two long sides, two narrow sides, an outer face and an inner face, and further comprising:

(i) a means for releasably fastening said front portion to said rear portion applied to said inner face of said rear portion at each of said two narrow sides whereby said means for releasably fastening is utilized when said diaper is worn by said toddler; and, (ii) a three-sided retractable flap having a perimeter defined by perforations through said rear portion and formed by a portion of the rear portion between said perforations, and centered between said two narrow sides and situated abutting one of said long sides and having an adhesive strip on [said] an outer face thereof permitting said retractable flap to be restrained in an up position attached to said outer face of the rear portion except for the outer face of the flap by said adhesive strip such that said toddler can sit on said toilet wearing said diaper having an exposed anal area, be tricked into depositing the fecal excrement into the toilet, be rewarded for doing so and thus favorably reinforce such depositing; and, (c) a crotch portion disposed between and integral with said rear portion and said front portion, and shaped such that toddler's legs may be disposed around said crotch portion.

* * * * *